(12) United States Patent
Aoyagi et al.

(10) Patent No.: US 8,974,816 B2
(45) Date of Patent: *Mar. 10, 2015

(54) WATER RESISTANT PATCH PREPARATION

(75) Inventors: Kazuhiro Aoyagi, Ibaraki (JP); Yoshihiro Iwao, Ibaraki (JP); Kensuke Matsuoka, Ibaraki (JP)

(73) Assignee: Nitto Denko Corporation, Ibaraki (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/872,447

(22) Filed: Aug. 31, 2010

(65) Prior Publication Data

US 2011/0059155 A1 Mar. 10, 2011

(30) Foreign Application Priority Data

Sep. 8, 2009 (JP) ................................ 2009-207563

(51) Int. Cl.
*A61K 9/70* (2006.01)
*A61F 13/02* (2006.01)
*A61F 13/00* (2006.01)

(52) U.S. Cl.
CPC ............... *A61F 13/023* (2013.01); *A61K 9/703* (2013.01); *A61K 9/7038* (2013.01); *A61F 2013/00651* (2013.01); *A61F 2013/0071* (2013.01)
USPC ........................... 424/443; 424/400; 424/447

(58) Field of Classification Search
CPC .... A61K 9/703; A61K 9/7023; A61K 9/7038
USPC .......................................... 424/443, 400, 447
See application file for complete search history.

(56) References Cited

U.S. PATENT DOCUMENTS

| 4,655,768 | A | * | 4/1987 | Marecki et al. ................ 424/448 |
| 4,906,169 | A | * | 3/1990 | Chien et al. .................... 424/448 |
| 4,909,244 | A | * | 3/1990 | Quarfoot et al. ................ 602/48 |
| 5,092,323 | A | * | 3/1992 | Riedel et al. .................... 602/54 |
| 5,429,591 | A | | 7/1995 | Yamamoto et al. |
| 5,503,844 | A | * | 4/1996 | Kwiatek et al. ................ 424/449 |
| 5,591,447 | A | * | 1/1997 | Jensen .......................... 424/443 |
| 5,976,117 | A | | 11/1999 | Dunshee et al. |
| 6,495,229 | B1 | | 12/2002 | Carte et al. |
| 8,273,370 | B2 | | 9/2012 | Harima et al. |
| 2003/0064190 | A1 | | 4/2003 | Carte et al. |
| 2005/0147564 | A1 | | 7/2005 | Drechsel et al. |
| 2007/0106195 | A1 | * | 5/2007 | Marcoux et al. ................ 602/57 |
| 2009/0022987 | A1 | | 1/2009 | Hashino et al. |
| 2009/0092819 | A1 | | 4/2009 | Malik et al. |
| 2010/0055162 | A1 | | 3/2010 | Harima et al. |

FOREIGN PATENT DOCUMENTS

| CN | 101347417 A | 1/2009 |
| JP | 05-503871 A | 6/1993 |
| JP | 06-000201 A | 1/1994 |
| JP | 09-110679 A | 4/1997 |
| JP | 09-124462 A | 5/1997 |
| JP | 2000-037413 A | 2/2000 |
| JP | 2009-045444 A | 3/2009 |
| WO | WO 94/14062 A1 | 6/1994 |
| WO | WO 01/19306 A1 | 3/2001 |
| WO | WO 2007/109593 A2 | 9/2007 |
| WO | WO 2008/142896 A1 | 11/2008 |
| WO | WO 2009/049008 A2 | 4/2009 |
| WO | 2009/085890 A2 | 7/2009 |

OTHER PUBLICATIONS

European Patent Office, European Search Report in European Patent Application No. 10251560.8 (Dec. 6, 2010).
Chinese Patent Office, First Office Action, in Chinese Patent Application No. 201010278022.6 (Feb. 21, 2013).
Japanese Patent Office, Notice of Reasons for Refusal in Japanese Patent Application No. 2009-207563 (Apr. 23, 2013).
European Patent Office, Extended European Search Report in European Patent Application in No. 10251560.8 (Dec. 6, 2010).
European Patent Office, Extended European Search Report in European Patent Application in No. 09168756.6 (Dec. 11, 2009).
United States Patent and Trademark Office, Non-Final Office Action in U.S. Appl. No. 12/548,550 (Jun. 23, 2011).
United States Patent and Trademark Office, Final Office Action in U.S. Appl. No. 12/548,550 (Jan. 3, 2012).
Japanese Patent Office, Notice of Reasons for Refusal in Japanese Patent Application No. 2009-207563 (Jul. 9, 2013).
Chinese Patent Office, Office Action in Chinese Patent Application No. 201010278022.6 (Dec. 13, 2013).
Chinese Patent Office, Office Action in Chinese Patent Application No. 201010278022.6 (May 21, 2014).

* cited by examiner

Primary Examiner — Rebecca Prouty
Assistant Examiner — Danielle Sullivan
(74) Attorney, Agent, or Firm — Leydig, Voit & Mayer, Ltd.

(57) ABSTRACT

The present invention provides a water resistant patch preparation having a central part and a peripheral part, which preparation is comprised of a support and an adhesive layer comprising a drug, which is formed on one surface of the support, wherein at least a part of a lateral end of the adhesive layer in the peripheral part is located inside a lateral end of the support, and the adhesive layer in the peripheral part has a thickness smaller than that of the adhesive layer in the central part.

18 Claims, 7 Drawing Sheets

(a)

(b)

(c)

(d)

WATER RESISTANT PATCH PREPARATION

TECHNICAL FIELD OF THE INVENTION

The present invention relates to a water resistant patch preparation comprising a support and an adhesive layer containing a drug which is laminated on at least one surface of the support.

BACKGROUND OF THE INVENTION

As a preparation for administering a drug to the body for the treatment or prophylaxis of a disease, for example, transdermal absorption type preparations can be mentioned, which can avoid drug metabolism due to the first-pass through the liver and various side effects, and can sustainably administer a drug for a long time. Among those, a patch preparation containing a drug in an adhesive has been developed, since an administration operation is easy and the dose can be strictly controlled.

In general, a patch preparation comprises a support made of a cloth, a plastic film and the like and an adhesive layer containing a drug, which is laminated on the support, and is provided with a release liner laminated on the adhesive layer and in a package made of a resin film and the like.

In recent years, a bulkier adhesive layer is often employed to maintain a large amount of a drug in an adhesive layer. As other characteristic of recent patch preparations, a soft adhesive layer tends to be employed such as an adhesive layer containing a large amount of a liquid component therein and the like, in an attempt to improve a soft feeling on adhesion to the skin, or reduce skin irritation due to detachment of stratum corneum during peeling. For such patch preparations, protrusion of the components of the adhesive layer from the edge of the adhesive patch, i.e., cold flow, poses problems during adhesion to the skin layer. Cold flow occurs depending on the property of the adhesive, and is often developed particularly when the adhesive layer is not crosslinked. In addition, it often occurs when a patch preparation is under a load for a long time, namely, when a patch preparation is contained in a package and stored for a long period and the like. Adverse influences of cold flow include, for example, degraded performance of taking out of a patch preparation from a package, which is caused by adhesion of protruded adhesive layer components to the inside of the package, attachment to clothes, edge lifting and staining of patch preparation during adhesion to the skin, lower effect of adhesive patch having a medicinal effect and the like.

A document working on such problems is, for example, patent document 1. In the cross sectional shape of the patch preparation of patent document 1, at least one part of a lateral end is located on the central part side of the patch preparation than the line segment perpendicularly drawn from a lateral end of a support to a release liner. However, since such a lateral end of an adhesive layer has a large exposed area, when it is soaked in water for a long time such as a bath and the like, a component such as a drug and the like may elute from the exposed lateral end of an adhesive layer of a patch preparation adhered to the skin, thus lowering the efficacy.

In addition, although not a drug-containing patch preparation, patent document 2 discloses a hydrocolloid dressing material having a smaller thickness in the peripheral part than in the central part, since the peripheral part is embossed. This document describes, "when the thickness of the peripheral part is too large, the edge of the peripheral part is easily peeled during application, and when it is too thin, sufficient adhesiveness to the skin surface cannot be ensured and wrinkles are easily developed during application". However, it does not describe or suggest that a lateral end of an adhesive layer in the peripheral part is located inside the lateral end of the support, nor does it teach the problems of decreased efficacy due to contact with water and the like.

PRIOR ART DOCUMENTS

Patent Documents patent document 1: JP-A-2009-45444
patent document 2: JP-A-2000-37413

SUMMARY OF THE INVENTION

Problems to be Solved by the Invention

The present invention has been made in view of such situation and aims to provide a water resistant patch preparation which suppresses cold flow and elution of components such as a drug and the like from the exposed lateral end of the adhesive layer when it is soaked in water for a long time such as a bath and the like.

Means of Solving the Problems

The present inventors have conducted intensive studies and found that an exposed area of an adhesive layer in the peripheral part can be minimized by setting the thickness of the adhesive layer in the peripheral part of a patch preparation smaller than the thickness of the adhesive layer in the central part, and placing a lateral end of the adhesive layer at a predetermined position and, as a result, surprisingly, cold flow can be suppressed and elution of a drug from the lateral end of the adhesive layer when it is soaked in water such as a bath and the like does not occur easily. Accordingly, the present invention encompasses the following.

[1] A water resistant patch preparation having a central part and a peripheral part, comprising: a support; and an adhesive layer containing a drug, the adhesive layer being formed on one surface of the support, wherein:

at least a part of a lateral end of the adhesive layer in the peripheral part is located inside a lateral end of the support, and a thickness of the adhesive layer in the peripheral part is smaller than that of the adhesive layer in the central part.

[2] The water resistant patch preparation of the above-mentioned [1], wherein the thickness of the adhesive layer in the aforementioned peripheral part is 1.5-150 μm.

[3] The water resistant patch preparation of the above-mentioned [1] or [2], wherein the difference between the maximum thickness of the adhesive layer in the aforementioned central part and the thickness of the adhesive layer in the aforementioned peripheral part is 20-2000 μm.

[4] The water resistant patch preparation of any of the above-mentioned [1] to [3], wherein the distance from a lateral end of the support to the most internal part of a lateral end of the adhesive layer in the peripheral part is 0.5-5 mm.

[5] The water resistant patch preparation of any of the above-mentioned [1] to [4], wherein the adhesive layer in the peripheral part is a band with a width of 0.5-5 mm.

[6] The water resistant patch preparation of any of the above-mentioned [1] to [5], wherein the aforementioned adhesive layer comprises an organic liquid component.

[7] The water resistant patch preparation of any of the above-mentioned [1] to [6], wherein the adhesive layer is crosslinked.

[8] The water resistant patch preparation of any of the above-mentioned [1] to [7], wherein the aforementioned support comprises a resin film and the aforementioned resin film has a thickness of 1-45 μm.

[9] The water resistant patch preparation of any of the above-mentioned [1] to [8], wherein the aforementioned support comprises a thermoplastic resin.

[10] The water resistant patch preparation of the above-mentioned [9], wherein the aforementioned thermoplastic resin comprises poly(ethylene terephthalate).

[11] The water resistant patch preparation of any of the above-mentioned [1] to [10], wherein a release liner is further laminated on the adhesive layer.

Effect of the Invention

The water resistant patch preparation of the present invention improves take-out performance of a patch preparation from a package by suppressing cold flow, and can prevent attachment to clothes, as well as edge lifting and contamination during application to the skin. Moreover, the water resistant patch preparation of the present invention can suppress elution of components such as a drug and the like from the exposed lateral end of the adhesive layer when it is soaked in water for a long time such as a bath and the like.

EMBODIMENT OF THE INVENTION

Figure 1:
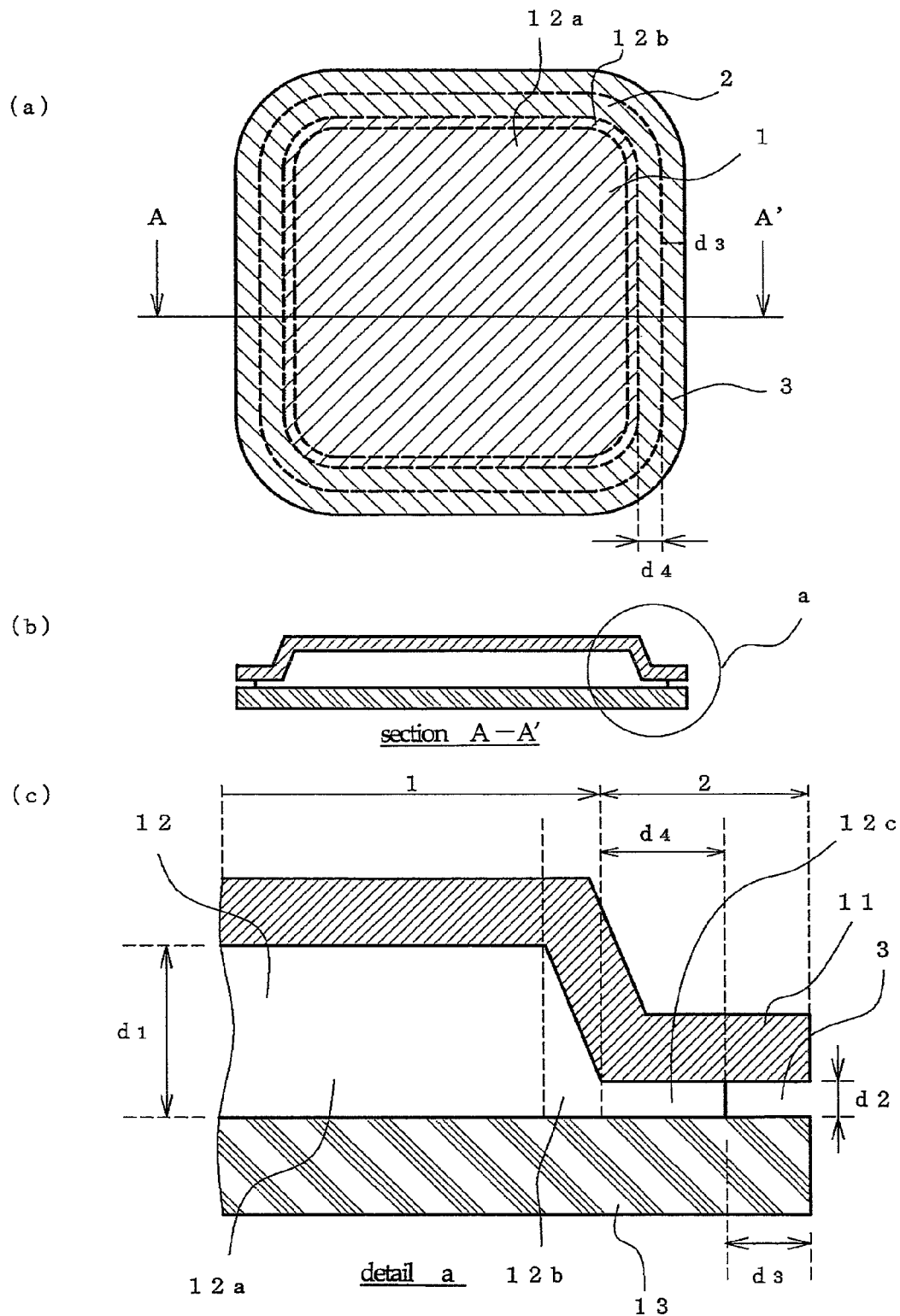
FIG. 1 shows a schematic plane view, a schematic sectional view and the detail thereof of one embodiment of the water resistant patch preparation of the present invention.

The present invention is explained in detail in the following by referring to the drawings. In the drawings, the dimensional size ratios of elements used to explicitly indicate each element are different from actual ratios.

FIG. 1 shows a schematic plane view (FIG. 1(a)), a schematic sectional view (FIG. 1(b)) and the detail thereof (FIG. 1(c)) of one embodiment of the water resistant patch preparation of the present invention. The water resistant patch preparation of the present invention has a support 11 and an adhesive layer 12 containing a drug, and may have a release liner 13 to be laminated on the adhesive layer 12 to protect an adhesive surface before adhesion to the skin.

The water resistant patch preparation of the present invention has a central part 1 and a peripheral part 2 thereof (FIG. 1(a)). Here, the peripheral part contacts the central part and is located around the central part.

In the peripheral part 2 is formed a thin film part 12c of the adhesive layer 12, and the adhesive layer 12 in the central part 1 consists of a thick film part 12a and a transition part 12b wherein the thickness of the adhesive layer 12 becomes smaller from the thick film part 12a to a thin film part 12c (FIG. 1(c)). A thickness $d_1$ of the thick film part 12a of the adhesive layer 12 in the central part 1 is, for example, 50-5,000 μm, preferably 100-4,000 μm. By employing the above-mentioned range, a decrease in the adhesiveness can be prevented more effectively, the shape of the adhesive layer 12 can be maintained, and cold flow can be more effectively suppressed by the present invention. The thickness $d_1$ of the thick film part 12a of the adhesive layer 12 is generally approximately constant.

A thickness $d_2$ of the thin film part 12c of the adhesive layer 12 in the peripheral part 2 is preferably 1.5 μm-150 μm to ensure required skin adhesive force and suppression of cold flow. It is also preferable that the thickness $d_2$ be approximately constant within the range of a width $d_4$. The film thickness being approximately constant means that the dispersion of the film thickness is within ±25%.

The water resistant patch preparation of the present invention is characterized in that the thickness $d_2$ of the adhesive layer 12 in the peripheral part 2 is smaller than the thickness $d_1$ of the adhesive layer 12 in the central part 1. The difference $(d_1-d_2)$ between the maximum thickness of the adhesive layer 12 in the central part 1 and that of the adhesive layer 12 in the peripheral part 2 is preferably 20-2,000 μm, more preferably 40-1,500 μm, so as to hold up package or clothes in the central part 1, reduce the frequency of rubbing of the edge of the patch preparation main body against package or clothes, and impart necessary adhesiveness to adhesive layer 12 in the central part 1.

Figure 9:
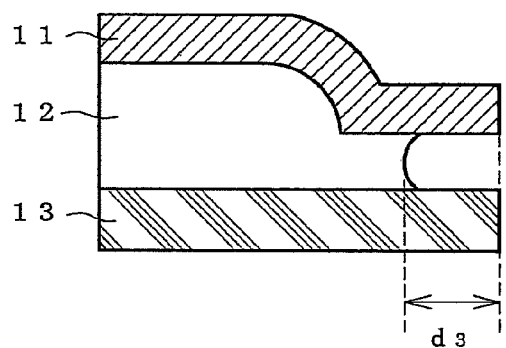
FIG. 9 shows schematic sectional views of patch preparations of Examples 1, 2 and Comparative Examples 1-6.
Figure 9:
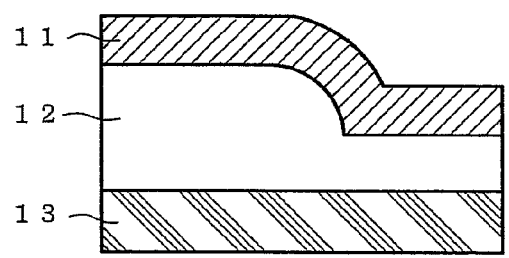
Figure 9:
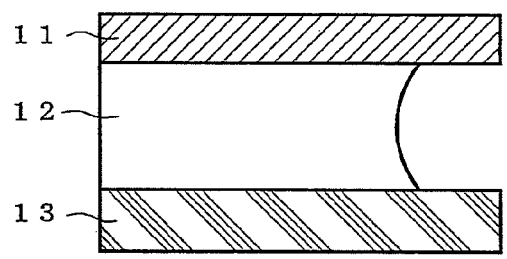
Figure 9:
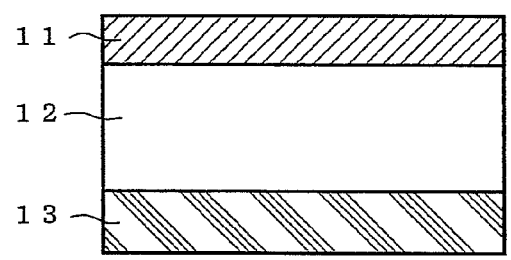

As shown in detail a (FIG. 1(c)) in FIG. 1, the patch preparation of the present invention is characterized in that at least a part of a lateral end of the adhesive layer 12 (thin film part 12c) in the peripheral part 2 is located at the central part 1 side (i.e., inside) of the patch preparation from a lateral end of the support 11. In other words, the peripheral part 2 of the patch preparation has a part free of an adhesive layer, where the adhesive layer 12 is not overlapped on the surface of the support 11 (hereinafter sometimes to be referred to as a void part 3). In the part where a lateral end of the adhesive layer 12 is located at the central part 1 side of the patch preparation than a lateral end of the support 11, the distance $d_3$ (width) from a lateral end of the support 11 to a lateral end of the adhesive layer 12 in the direction parallel to an exposed surface of the support (hereinafter to be also referred to as "width of void part 3") is preferably 0.5-5 mm, more preferably 1-5 mm, to minimize an influence of the external environment on the adhesive layer. When the cross section of the lateral end of the adhesive layer is perpendicular to the release liner 13 as shown in FIG. 1(c), a width $d_3$ of a void part 3 is the same in any position in the cross section direction of a lateral end. When the cross section of a lateral end is a concave (concave face) as shown in FIG. 9(a) mentioned below, the width of the void part 3 between the most internal part near the central part of the cross section and a lateral end of a support is the width $d_3$. In the patch preparation of the present invention, the void part 3 is preferably foamed over 1-100% of the full-length of the outer circumference of the patch preparation (support 11), more preferably, over the entirety of the outer circumference of the patch preparation (support 11) as shown in FIG. 1(*a*).

In the part having the adhesive layer 12 in the peripheral part 2, a width $d_4$ of the adhesive layer 12 in the peripheral part preferably has a band of 0.5-5 mm, more preferably 0.5-3 mm, as shown in FIG. 1(*c*). By setting the width $d_4$ to fall within the above-mentioned range, cold flow can be suppressed more effectively, and a decrease in the adhesive force of the peripheral part 2 can be more effectively prevented. As shown in FIG. 1(*c*), the boundary between the width $d_4$ of the adhesive layer and the central part is the boundary between the transition part 12*b* and the thin film part 12*c*. To sufficiently achieve the effect of the present invention, each peripheral part of the patch preparation preferably has such a band-shaped part.

Figure 2:
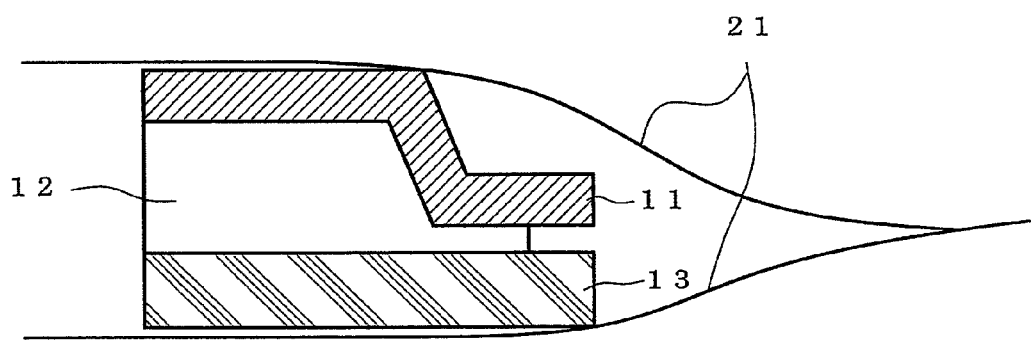
FIG. 2 is a schematic sectional view showing one embodiment of the water resistant patch preparation of the present invention, which is contained in a package.
Figure 3:
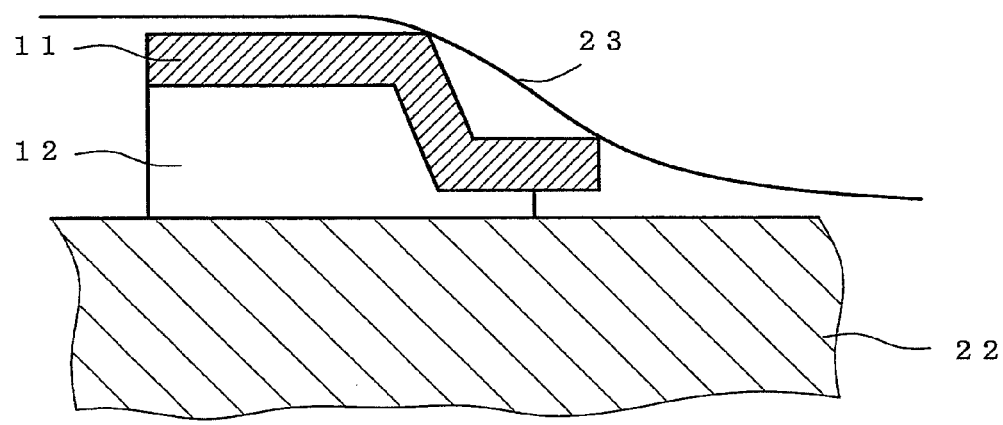
FIG. 3 is a schematic sectional view showing one embodiment of the water resistant patch preparation of the present invention, which is adhered to the skin.
Figure 4:
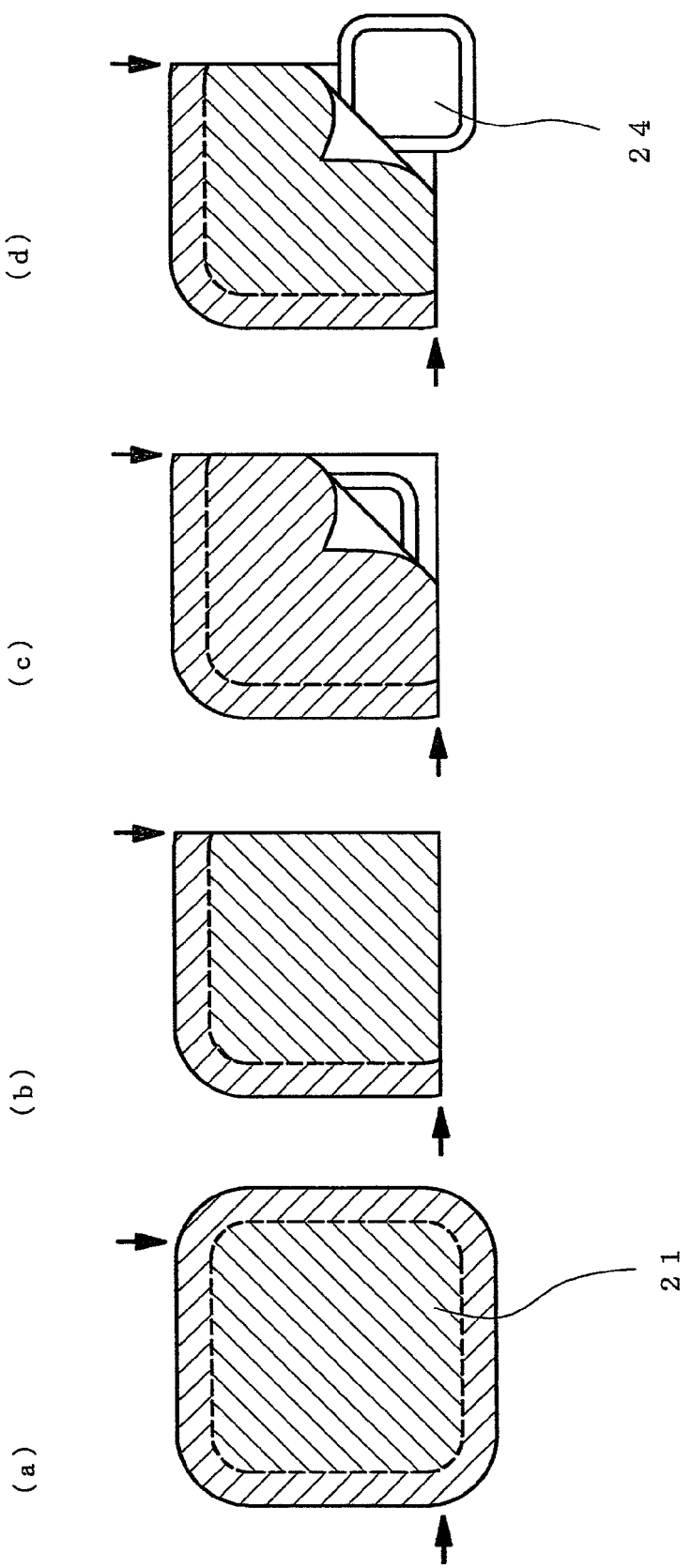
FIG. 4 is a schematic view showing the manner of taking out one embodiment of the water resistant patch preparation of the present invention from the package.

FIG. 2 is a schematic sectional view showing one embodiment of the water resistant patch preparation of the present invention, which is contained in a package 21. FIG. 3 is a schematic sectional view showing one embodiment of the water resistant patch preparation of the present invention, which is adhered to the skin 22. FIG. 4 is a schematic view showing one example of taking out the water resistant patch preparation 24 of the present invention, which is contained in a package 21, including breaking a seal of two sides of a package (FIG. 4(*a*)) with scissors or along a V-shaped notch (FIG. 4(*b*), (*c*)), and taking out the water resistant patch preparation of the present invention 24 contained in a package 21 (FIG. 4(*d*)).

In the water resistant patch preparation of the present invention, since the thickness of the adhesive layer in the peripheral part 2 is smaller than that of the adhesive layer in the central part 1, the frequency of contact of a lateral end of the patch preparation with an inner surface of a package 21 or clothes 23 reduces and adhesion to an inner surface of the package 21 or clothes 23 can be prevented (FIG. 2 and FIG. 3). In addition, since a pressure is not easily applied to a lateral end of the patch preparation, cold flow can be effectively suppressed. As a result, the patch preparation 24 can be taken out from a package more smoothly (FIG. 4). Furthermore, since an adhesive layer lateral end in the peripheral part is located inside the support lateral end (i.e., central part side), cold flow can be more effectively suppressed. Also, when a water resistant patch preparation is detached from the skin 22, a support lateral end can be easily held with fingers, thus rendering detachment easier.

Figure 5:
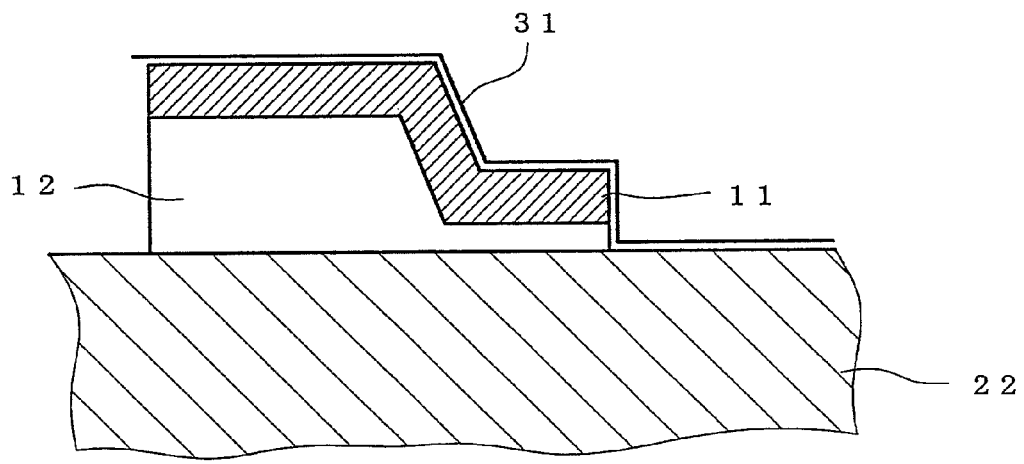
FIG. 5 is a schematic sectional view showing the positional relationship between a conventional patch preparation and water.
Figure 6:
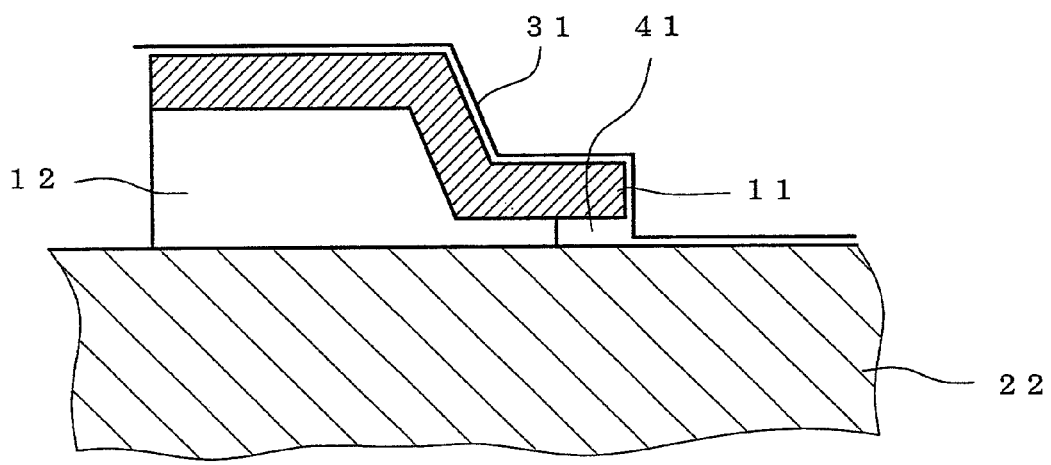
FIG. 6 is a schematic sectional view showing the positional relationship between one embodiment of the water resistant patch preparation of the present invention and water.

FIG. 5 and FIG. 6 schematically show an example of penetration of water 31 into a lateral end of a water resistant patch preparation during bathing of a person carrying the patch preparation adhered to the skin 22. FIG. 5 is a schematic sectional view showing the positional relationship between a conventional patch preparation and water 31, and FIG. 6 is a schematic sectional view showing the positional relationship between one embodiment of the water resistant patch preparation of the present invention and water 31. In FIG. 5, water 31 can easily contact a lateral end of an adhesive layer 12 of the patch preparation, and contact frequency is high. On the other hand, in FIG. 6, water 31 cannot easily contact a lateral end of an adhesive layer 12 of a water resistant patch preparation, and contact frequency is low. Such effect is believed attributable to the difficulty for water to physically and chemically access a lateral end of the adhesive layer 12 due to the air present in a void 41 between a lateral end of the support 11 and a surface of the skin 22 and also hydrophobicity of the support 11 in the lateral end of a water resistant patch preparation.

(Adhesive Layer)

Now, a production method of a composition for foaming an adhesive layer and the amounts of components are explained. The amount of each component described in the following is a ratio in wt % of the amount of each component relative to the amount of whole components except solvent.

The adhesive layer can be formed by mixing an adhesive with components such as a drug, a tackifier, an organic liquid component and the like as necessary in the presence of a solvent to give a composition, forming layers thereof by a method such as coating and the like, and drying the layers. The adhesive layer is preferably a hydrophobic adhesive layer in view of adhesion to the skin, and therefore, an anhydrous adhesive layer is preferable. From such aspect, the solvent is preferably an organic solvent.

While the organic solvent is not particularly limited, one having compatibility with the aforementioned respective components constituting the adhesive layer and easily volatilizable during a drying process is preferable. Examples of the organic solvent include aromatic hydrocarbons such as toluene, xylene and the like, aliphatic hydrocarbons such as hexane and the like, esters such as ethyl acetate and the like, alcohols such as ethanol and the like, ethers such as diethyl ether, tetrahydrofuran, etc. and the like. These may be used alone or in a mixture of two or more kinds thereof in combination.

The aforementioned drying may be performed by air-drying, or according to a known method using a dryer, hot air, far-infrared radiation and the like.

While the method of mixing the aforementioned respective components is not limited, examples thereof include kneading machines such as a kneader, a planetary mixer and the like, dispersion machines such as a homogenizer and the like, stirring machines such as a propeller-type blade stirring machine, etc. and the like. These can be used alone or in a combination of two or more kinds thereof.

While the adhesive constituting the adhesive layer is not particularly limited, acrylic adhesives and rubber based adhesives are particularly preferably used in view of skin adhesiveness and the like.

The adhesive layer may be a crosslinked adhesive layer obtained by a cross-linking treatment or a non-crosslinked adhesive layer obtained without a cross-linking treatment. Here, the cross-linking treatment refers to a known treatment that applies crosslinking to an adhesive layer so as to simultaneously achieve sufficient maintenance of skin adhesiveness of the patch preparation, and suppression of skin irritation to a low level, which is caused by stretching the skin and physically scraping the stratum corneum of the skin to peel off the patch preparation from the skin surface. Examples of the cross-linking treatment include a chemical crosslinking treatment, a treatment for ion cross-linking, and a physical crosslinking treatment using electron beam, ultraviolet light and the like. Examples of the crosslinking agent include organic metal salts such as zinc acetate and the like, metal alcoholate, metal chelate compound, an epoxy compound, an amide compound, an amine compound, acid anhydride, organic peroxide, an isocyanate compound and the like.

When the adhesive layer is a non-crosslinked adhesive layer, and the adhesive layer contains a rubber based adhesive, cold flow tends to occur. The water resistant patch preparation of the present invention is advantageous in that cold flow can be effectively suppressed even when the adhesive layer is a non-crosslinked adhesive layer, and the adhesive layer contains a rubber based adhesive.

The above-mentioned acrylic adhesive is comprised of an acrylic polymer, and examples of the acrylic polymer include alkyl (meth)acrylate homopolymers and copolymers thereof. Here, alkyl of alkyl (meth)acrylate is preferably straight chain or branched chain alkyl having a carbon number of 4-12. Specific examples of the alkyl (meth)acrylate include butyl (meth)acrylate, t-butyl (meth)acrylate, pentyl (meth)acrylate, hexyl (meth)acrylate, heptyl (meth)acrylate, octyl (meth) acrylate, isooctyl (meth)acrylate, nonyl (meth)acrylate, isononyl (meth)acrylate, decyl (meth)acrylate, undecyl (meth)acrylate, dodecyl (meth) acrylate, 2-ethylhexyl (meth) acrylate, and the like. The proportion of alkyl (meth)acrylate to be polymerized is preferably not less than 50 wt %, more preferably not less than 60 wt %, of the monomers constituting the acrylic polymer. While the monomer to be copolymerized with alkyl (meth)acrylate is not particularly limited, for example, (meth)acrylic acid and the like can be mentioned.

The proportion of acrylic adhesive to be added is preferably 30-95 wt %, more preferably 40-90 wt %, of the adhesive. When it is less than 30 wt %, adhesive force and cohesion strength become insufficient, and when it exceeds 95 wt %, the drug amount decreases relatively and sufficient efficacy is difficult to achieve.

Examples of the rubber based adhesive include polyisobutylene, polyisobutylene-polybutene based rubber, styrene-diene-styrene block copolymer, styrene-butadiene based rubber, nitrile based rubber, chloroprene based rubber, vinylpyridine based rubber, polyisobutylene based rubber, butyl based rubber, isoprene-isobutylene based rubber and the like. Among these, polyisobutylene, styrene-diene-styrene block copolymer [e.g., styrene-butadiene-styrene block copolymer (SBS), styrene-isoprene-styrene block copolymer (SIS) etc.] and the like are preferably used in view of solubility of medicament and skin adhesiveness, and they may be used in a mixture.

To achieve appropriate adhesive force and solubility of drugs, a rubber based adhesive can be a mixture of the same component or different components having different average molecular weights. To explain with polyisobutylene as an example, a mixture of high molecular weight polyisobutylene having a viscosity average molecular weight of 1,800,000-5,500,000, medium molecular weight polyisobutylene having a viscosity average molecular weight of 40,000-85,000 and, where necessary, lower molecular weight polyisobutylene is preferable. The viscosity average molecular weight in the present invention is determined by calculating a Staudinger index ($J_0$) according to the Schulz-Blaschke equation from the flow time of capillary 1 of Ubbelohde viscometer at 20° C., and from the following formula using the obtained $J_0$ value:

$$J_0 = \eta_{sp}/c(1+0.31\,\eta_{sp}) \text{ (by Schulz-Blaschke equation)}$$

wherein $\eta_{sp} = t/t_0 - 1$ t: flow time of solution (by Hagenbach-couette Correction formula)

$t_0$: flow time of solvent (by Hagenbach-couette Correction formula)

c: concentration of solution (g/cm³)

$$J_0 = 3.06 \times 10^{-2}\, Mv^{0.65}$$

wherein Mv: viscosity average molecular weight

Here, a polyisobutylene mixture preferably contains high molecular weight polyisobutylene in a proportion of 10-80 wt %, preferably 10-50 wt %, medium molecular weight polyisobutylene in a proportion of 0-90 wt %, preferably 10-80 wt %, and low molecular weight polyisobutylene in a proportion of 0-80 wt %, preferably 0-60 wt %. A generally obtained adhesive layer becomes stiff when the proportion of a high molecular weight component increases, and soft when the proportion of a low molecular weight component increases.

To confer an adequate adhesiveness to the adhesive layer, for example, a tackifier such as rosin based resin, polyterpene resin, chroman-indene resin, petroleum based resin, terpene-phenol resin, xylene resin and the like may be added. These may be used alone or in a mixture of two or more kinds thereof. Examples of the aforementioned petroleum based resin include aliphatic series (C5 series) petroleum resin, aromatic series (C9 series) petroleum resin, copolymer series (C5-C9 series) petroleum resin and alicyclic saturated hydrocarbon resin obtained by partially or completely hydrogenating aromatic series (C9 series) petroleum resin. As the alicyclic saturated hydrocarbon resin, one having a softening point (ring and ball method) of 90-150° C. is preferable. While the amount of the tackifier is not limited, it is, for example, 10-40 wt % so as to impart appropriate adhesiveness and prevent saturation of the effect of a tackifier due to an increased amount thereof.

The water resistant patch preparation of the present invention contains a drug in an adhesive layer. The drug here is not particularly limited, and a transdermally absorbable drug that can be administered to mammals such as human and the like through the skin is preferable. Specific examples of such drug include general anesthetics, hypnotic sedatives, antiepileptic drugs, antipyretic analgesic antiphlogistic drugs, anti-vertiginous drugs, psychoneurotic drugs, topical anesthetics, skeleton muscle relaxants, autonomic drugs, antispasmodic drugs, anti-parkinsonian drugs, anti-histamine drugs, cardiac stimulants, drugs for arrhythmia, therapeutic drugs for angina pectoris, diuretic, hypotensive drug, vasoconstrictor, coronary vasodilator, peripheral vasodilators, arteriosclerosis drugs, drugs for circulatory organ, anapnoics, bronchodilator, antitussive expectorant, hormone drugs, external drugs for purulent diseases, analgesic-antipruritic-styptic-antiinflammatory drugs, drugs for parasitic skin diseases, hemostatic drugs, gout treatment drugs, drugs for diabetes, anti-malignant tumor agents, antibiotic, chemical therapy agents, narcotic, quit smoking aids and the like.

The proportion of the drug in the adhesive layer is not particularly limited as long as it affords the effect of a transdermally absorbable drug and does not impair the adhesive property of the adhesive. It is preferably 0.1-60 wt %, more preferably 0.5-40 wt %, relative to the total weight of the adhesive layer (when the adhesive layer contains a crosslinking agent, the weight of the crosslinking agent is excluded). When it is less than 0.1 wt %, the treatment effect may be insufficient, and when it exceeds 60 wt %, irritation to the skin may occur and may become economically disadvantageous.

When desired, the adhesive layer can contain an organic liquid component. The organic liquid component is not particularly limited, and examples thereof include glycols such as ethylene glycol, diethylene glycol, propylene glycol, dipropylene glycol, tripropylene glycol, triethylene glycol, poly(ethylene glycol), poly(propylene glycol) and the like; fats and oils such as olive oil, castor oil, lanolin and the like; hydrocarbons such as squalane and liquid paraffin; various surfactants; ethoxylated stearyl alcohol; glycerol monoesters such as oleic acid monoglyceride, caprylic acid monoglyceride and lauryl acid monoglyceride; dialkyl ester of polyalkylene glycol such as poly(propylene glycol); glycerol diester such as glycerol diacetate and the like, glycerol triester such as glycerol triacetate and the like, or a mixture thereof; fatty acid alkyl ester such as triethyl citrate and the like; long chain alcohol; higher fatty acid such as oleic acid and caprylic acid; alkyl ester of higher fatty acid such as isopropyl myristate and isopropyl palmitate; pyrrolidones such as N-methylpyrrolidone and N-dodecylpyrrolidone; sulfoxides such as decyl methyl sulfoxide; 1,3-butanediol and the like. These can be used alone or in a mixture of two or more kinds thereof.

An organic liquid component can be added to an adhesive layer in a proportion of preferably 0-60 wt %, more preferably 10-60 wt %, most preferably 20-60 wt %. Generally, when it is blended in a proportion of not less than 10 wt %, the adhesive layer is easily plasticized and cold flow occurs easily. Therefore, the present invention capable of effectively suppressing cold flow is particularly advantageous when an organic liquid component is contained. When it is blended in a proportion exceeding 60 wt %, the adhesive layer may face difficulty in maintaining a given shape.

(Support)

While the support is not particularly limited, one through which a drug and the like are substantially impermeable, namely, one through which an active ingredient, an additive and the like in the adhesive layer are less likely to permeate and be lost from the back face thereof to decrease the content is preferable.

Specifically, a single layer film comprised of a resin film such as polyethylene based film, polypropylene based film, polyester based film, polyvinyl acetate based film, ethylene/vinyl acetate copolymer film, polyvinyl chloride based film, polyurethane based film and the like, a metal foil such as aluminum foil, tin foil and the like, non-woven fabric, woven fabric, paper and the like, a laminate film thereof and the like can be used.

When a laminate of a porous material and a resin film is used as a support, an adhesive layer is laminated on the porous material side of the laminate. The porous material has concave and convex on the surface, and the concave and convex are considered to suppress movement or disappearance of voids (foams) contained in the adhesive layer. Using a porous material, therefore, cold flow can be suppressed. Moreover, when a porous material is used, since it has voids (foams) which move to an adhesive layer of a peripheral part of a patch preparation, and are fused with foams in the adhesive layer to form larger foams in the peripheral part, the effect of the present invention is considered to be enhanced. Since an adhesive layer component that flows out from a lateral end of a patch preparation can enter the space in the foams, the foams can effectively suppress the cold flow. When a support in such form is used, the cold flow-suppressive effect of the present invention is further enhanced, and water resistance is improved.

Examples of the porous material include a porous film and a sheet. When the sheet refers to one having a thickness of not less than 200 μm, a porous film is more preferable. The aforementioned porous film may be a single layer film or a laminate film and a film having an anchoring force to suppress movement of an adhesive layer is preferably used. Specific examples include paper, woven fabric, non-woven fabric, knitted fabric, film and metal foil mechanically subjected to a perforation treatment, and laminates thereof and the like. Of these, paper, woven fabric, non-woven fabric, and laminates thereof are preferable from the aspects of handling property and the like, and non-woven fabric is particularly preferable.

The resin film may be a single layer film or a laminate film, and a non-porous film made of a resin, which is impermeable to active ingredient, is preferable.

The porous film and the resin film may be made of similar materials or different materials. These films can be laminated by a known method and, as long as the effect of the present invention and the effect of the patch preparation are not impaired, various additives such as antioxidant, pigment, antistatic agent and the like may be appropriately added, and a treatment such as corona discharge treatment, UV-irradiation treatment and the like may be applied to the surface.

Examples of the materials of the porous film and resin film constituting the support include polyester, nylon, saran (registered trade mark of Asahi Kasei Corporation, The Dow Chemical Company), polyethylene, polypropylene, polyvinyl chloride, ethylene-ethyl acrylate copolymer, polytetrafluoroethylene, Surlyn (registered trade mark of Du Pont), combination of these and the like.

Such resin film has an action to suppress permeation of an adhesive layer component through back face of a support to decrease the content, and is preferably used to achieve what is called an occlusive dressing therapy (ODT) effect when the adhesive layer contains a drug.

When a production method comprising pressing and heating of an area corresponding to the peripheral part of the patch preparation main body is employed, the materials of the support, particularly the materials of the porous film and the resin film constituting the support, are preferably those from the aforementioned materials, which are deformed after being softened by heating, and maintain the deformed shape after cooling. Specifically, thermoplastic resin, for example, polyester, polypropylene, polyethylene and the like are preferable, and polyester, for example, poly(ethylene terephthalate) (hereinafter to be abbreviated as "PET") is particularly preferable.

The thickness of the porous film is preferably 10-100 μm in view of improvement of anchoring force, flexibility and adhesion operability of the whole patch preparation and the like. When woven fabric or non-woven fabric is used as a porous film, the basis weight is preferably 5-50 g/m², more preferably 10-30 g/m², to ensure foams with effective size and anchor property.

In the present invention, the thickness of the porous film is measured by staining a patch preparation with aqueous ruthenium acid solution, cutting the film with a freezing microtome, imaging the cut surface by FE-SEM (Hitachi, S-4800) at magnification 50-1,000 times and reading the gauge scales. In this case, concaves and convexes are present on the surface of the porous film. In a sectional image, 10 convexes are selected at random, and an average of the thickness of the porous film at the convexes is calculated and taken as the thickness of the porous film.

In the present invention, the basis weight of the porous film is determined by multiplying the thickness of the above-mentioned porous film by the specific gravity (apparent specific gravity) of the porous film and calculating the basis weight of the porous film.

While the thickness of the resin film is not particularly limited, it is preferably 1-45 μm. When it is less than 1 μm, destruction occurs during heating and pressurization, possibly resulting in insufficient strength during application. When it exceeds 45 μm, the rigidity of the resin film possibly develops an uncomfortable feeling during application to the skin. In the present invention, the thickness of the resin film is measured in the same manner as for the above-mentioned porous film.

Thus, a desirable support in the present invention is a laminate film of a polyester film with 1-45 μm thickness (preferably, PET film) and a non-woven fabric made of polyester (preferably, PET) having a basis weight of 10-30 g/m².

In consideration of the skin-following ability and comfortableness during application of a patch preparation, the thickness of the laminated support is preferably 5-200 μm.

(Release Liner)

A release liner to protect the adhesive surface can be laminated on the adhesive layer before applying the patch preparation to the skin. The material of the release liner is not particularly limited, and examples thereof include those known per se in the field. Specific examples thereof include resin films such as polyester such as PET, polyvinyl chloride, polyvinylidene chloride, various acrylic and methacrylic polymers, polystyrene, polycarbonate, polyimide, acetyl cellulose, regenerated cellulose (cellophane), celluloid and the like, a laminate film of high-quality paper, glassine paper and the like and polyolefin and the like. For safety, economic efficiency and drug-transfer properties, a polyester film is preferably used.

The release liner is preferably treated for easy peeling on the interfacial surface side with an adhesive, so as to facilitate peeling from the adhesive layer. While the easy peeling treatment is not limited, a known method can be applied. For example, a treatment for forming a peeling-treated layer using a release agent containing a curable silicone resin as a main component by a coating method such as bar coating, gravure coating and the like can be applied.

The thickness of the peeling-treated layer is preferably 0.01-5 μm to ensure release property and uniformity of the coating. The thickness of the release liner having a peeling-treated layer is generally 10-200 μm, preferably 50-100 μm, from the aspect of handling property.

The flat plane shape of the patch preparation of the present invention is not particularly limited and may be, for example, substantially rectangle, ellipse, circular shape and the like, in addition to the substantial square shown in FIG. 1. Here, the "substantially square" and "substantially rectangle" mean that the corner of the square and the corner of the rectangle do not for a right angle but are round as shown in FIG. 1. The size (area in planar view) of the patch preparation is not particularly limited. The area in planar view of the central part is preferably 100-10,000 mm$^2$, more preferably 100-5,000 mm$^2$.

(Production Method)

The patch preparation of the present invention can be produced, for example, by the following method.

To make the thickness of an adhesive layer of a peripheral part of a patch preparation smaller than that of an adhesive layer in the central part, a step of pressing the peripheral part of the patch preparation can be employed. Moreover, to produce a patch preparation free of an adhesive layer on a lateral end of the patch preparation, for example, (i) a pattern coating wherein an adhesive layer is not applied to the area corresponding to a lateral end of the patch preparation when coating a support or a release liner with the adhesive layer, and (ii) a method wherein an adhesive layer in an area corresponding to a lateral end of the patch preparation is removed after coating a support or a release liner with the adhesive layer, can be mentioned.

The water resistant patch preparation of the present invention can be efficiently produced by a method comprising, for example, (a) a step of preparing an adhesive sheet wherein an adhesive layer is laminated on a support, and a release liner is laminated on the adhesive layer; and (b) a first-pressing step including pressing an area of the adhesive sheet to be a peripheral part of the patch preparation with a first-press mold at a first-temperature from the support side to give a first-pressed adhesive sheet.

Preferably, subsequent to step (b), (c) a second-pressing step including pressing the whole or a part of the area in the obtained first-pressed adhesive sheet, which is to be a peripheral part of a patch preparation, with a second-press mold at a second-temperature lower than the first-temperature is performed. A part of the area to be the peripheral part is preferably an outer edge of the area to be the peripheral part.

Figure 7:
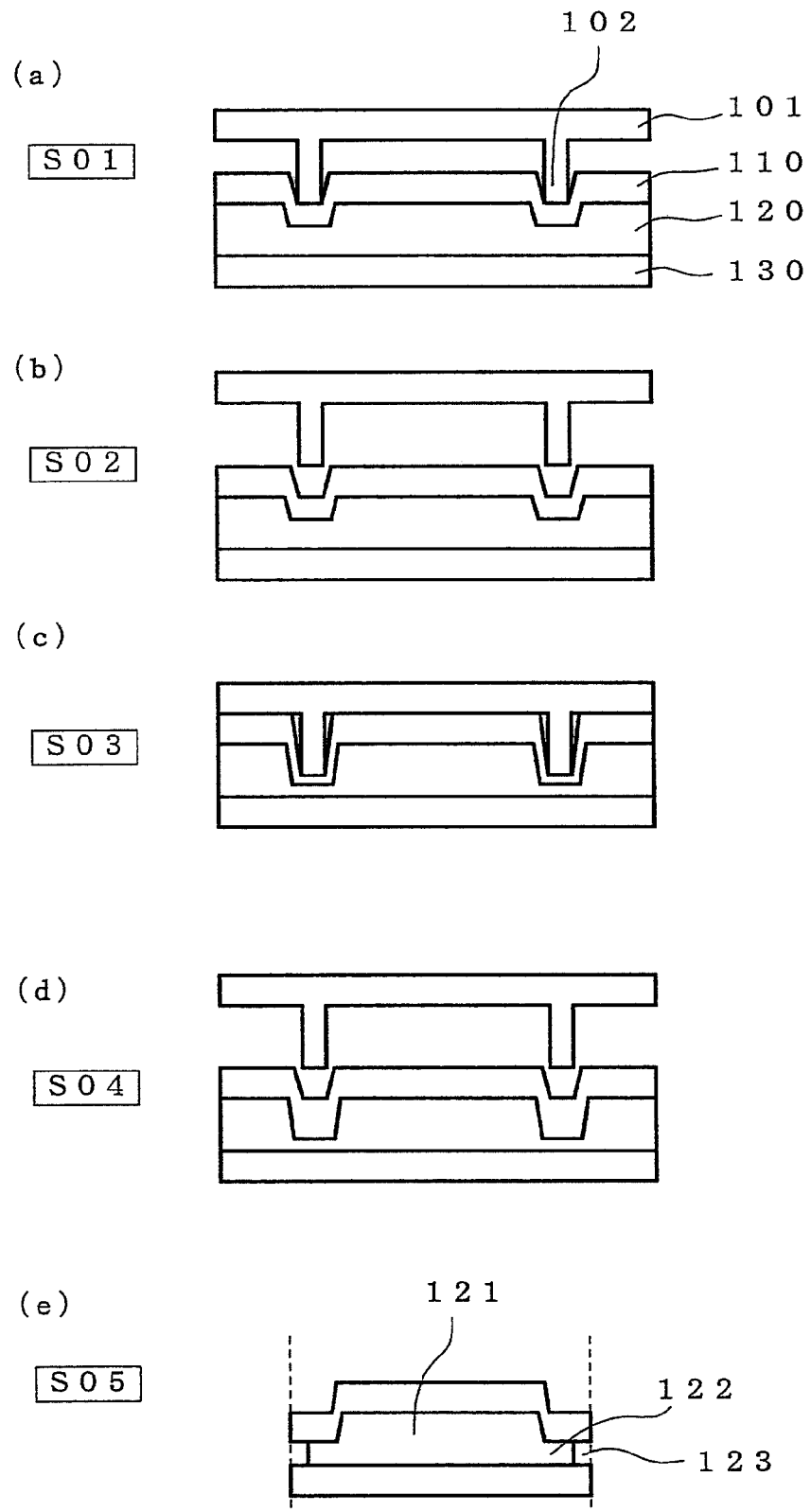
FIG. 7 shows one embodiment of formation step of a peripheral part.
Figure 8:
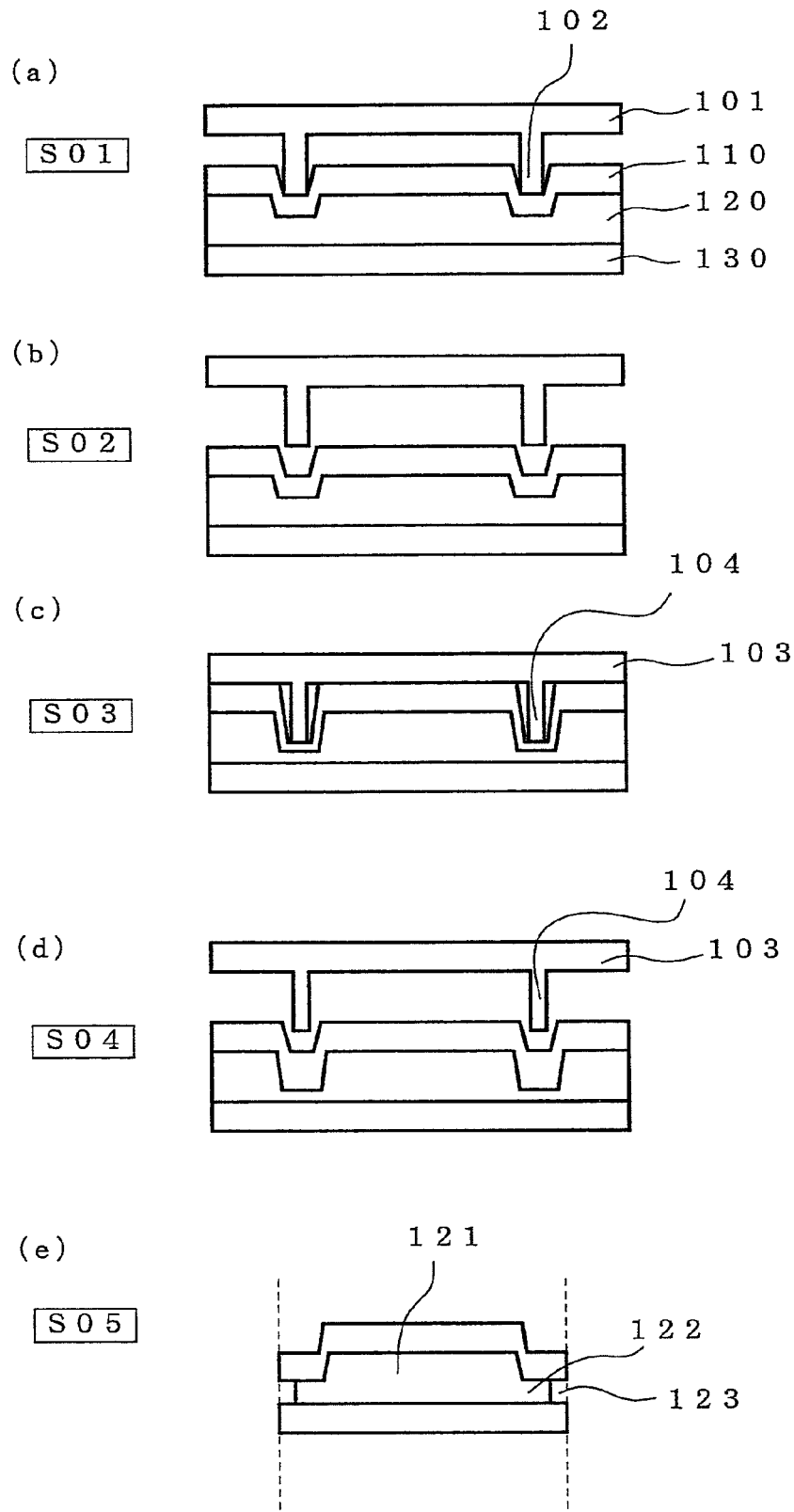
FIG. 8 shows another embodiment of formation step of a peripheral part.

The above-mentioned steps are schematically explained in FIG. 7 or FIG. 8.

A cutting step is preferably performed after the second-pressing step. The shape of the press mold only needs to be substantially flat in the surface facing a support, and the flat plane shape only needs to correspond to the peripheral part of the patch preparation. Specifically, for example, when the flat plane shape of the patch preparation is substantially rectangle, the flat plane shape of the press mold is defined by coaxial two rectangles.

The process shown in FIG. 7 is explained.

A laminate comprising a support 110, an adhesive layer 120 and a release liner 130 is placed on a stand (not shown) with the support 110 side facing upward. Using a press mold 101, the laminate is pressed from the support 110 side at a high temperature (first-pressing step S01, FIG. 7(a)). The press mold 101 has a convex part 102 having a rectangular cross section with predetermined width and height and, in a plane view, the shape of the inner periphery of the convex part 102 is substantially the same as that of the central part 121 of an adhesive. In the first-pressing step S01, since the adhesive layer 120 and the support 110 are pressed at a high temperature, the pressed shape is mostly maintained even after release of pressure by the press mold 101 (first-pressing releasing step S02, FIG. 7(b)). Next, the same part is strongly pressed again at around ambient temperature using the same press mold 101 (second-pressing step S03, FIG. 7(c)). When the second-pressing is released (second-pressing releasing step S04, FIG. 7(d)), the restoring force of the support 110 acts in an attempt to restore the shape of the support 110 at the first-pressing releasing step S02. When the substantially central part of the pressed part is cut in this state, an adhesive 120 in the peripheral part is drawn in the direction toward the central part 121 due to the restoring force of the support 110. As a result, a part of the adhesive 120 in the peripheral part 122 is drawn inside a lateral end surface of the support 110, forming a void part 123 (after cutting S05, FIG. 7(e)).

In FIG. 8, a convex part 104 thinner in the width direction than the convex part 102 of the press mold 101 used in the first-pressing step S01 is used as a second press mold 103 to be used in the second-pressing step S03. The shape of the adhesive in the peripheral part can also be controlled by changing the shape of the press mold between the first-pressing step S01 and the second-pressing step S03.

<Conditions of First-Pressing Step (Molding Support to Have Embossed Shape)>

A first-temperature of the press mold is preferably 80-200° C., more preferably 90-180° C. When it is not less than 80° C., the peripheral part of a patch preparation to be heated and pressed, as well as the support in the adjacent area thereof are softened by heat to enable molding into a desired embossed shape. Since it is not more than 200° C., an excess thermal load on the support, adhesive layer and release liner in the peripheral part of a patch preparation to be heated and pressed can be suppressed.

The pressure to be applied is preferably $1.0 \times 10^3$-$1.0 \times 10^9$ N/m$^2$, more preferably $1.0 \times 10^5$-$5.0 \times 10^7$ N/m$^2$. When it is not less than $1.0 \times 10^3$ N/m$^2$, the peripheral part of a patch preparation to be heated and pressed, as well as the support in the adjacent area thereof can be molded to have a desired embossed shape. Since it is not more than $1.0 \times 10^9$ N/m$^2$, an excess mechanical load on the support in the peripheral part of a patch preparation to be heated and pressed can be suppressed.

The pressing time is preferably 0.01-5 seconds, more preferably 0.05-3 seconds. With the above-mentioned range, the support in the peripheral part of a patch preparation can be certainly molded to have a desired shape, and an excess thermal load on the peripheral part of a patch preparation to be heated and pressed, as well as an adhesive layer in the adjacent area thereof can be suppressed. In addition, it is also preferable from the aspect of production efficiency.

When embossing, the distance between the press mold and the stand carrying a patch preparation is preferably approximately the same as (thickness of support+thickness of adhesive layer in the peripheral part+thickness of release liner). In consideration of the dispersion in the thicknesses of the support and release liner, however, it may be (thickness of support+thickness of adhesive layer in the peripheral part+thickness of release liner)±10 μm. With the above-mentioned range, the support in the peripheral part of a patch preparation can be certainly molded to have a desired shape, and an adhesive layer in the peripheral part of a patch preparation can have a desired thickness.

<Embossing Conditions of the Second-Pressing Step (Removal of Adhesive Layer from Lateral End of Peripheral Part)>

The second-temperature of the press mold is preferably 15-50° C., which is around ambient temperature. With the above-mentioned range, a thermal load on the peripheral part of a patch preparation to be pressed, as well as an adhesive layer in the adjacent area thereof can be suppressed, and excessive molding of the support molded to have a desired shape in the first-pressing step can be suppressed.

The pressure to be applied is preferably $1.0 \times 10^3$-$1.0 \times 10^9$ N/m$^2$, more preferably $1.0 \times 10^5$-$5.0 \times 10^7$ N/m$^2$. Since it is not less than $1.0 \times 10^3$ N/m$^2$, an adhesive layer in the peripheral part of a patch preparation to be pressed can be efficiently removed. Since it is not more than $1.0 \times 10^9$ N/m$^2$, an excess mechanical load on the support and release liner in the peripheral part of a patch preparation to be pressed can be suppressed.

The pressing time is preferably 0.1-10 seconds, more preferably 0.5-5 seconds. With the above-mentioned range, an adhesive in the peripheral part of a patch preparation can be certainly removed. In addition, it is also preferable from the aspect of production efficiency.

The distance between the press mold and stand thereof when embossing is preferably approximately the same as (thickness of support+thickness of release liner). In consideration of the dispersion in the thicknesses of the support and release liner, however, it may be (thickness of support+thickness of release liner)±10 μm. With the above-mentioned range, the adhesive in the peripheral part of a patch preparation can be certainly removed, and an excess mechanical load on the support and release liner can be suppressed.

The cutting means is not particularly limited, and laser, press-cutting blade and the like can be employed. Since adjustment of cutting size and position adjustment are easy and a clear end surface can be obtained, an original sheet is preferably punched out and punching out using a press-cutting blade dies set (male type and female type) is more preferable.

EXAMPLES

The present invention is explained in more detail in the following by referring to Examples and Comparative Examples, which are not to be construed as limitative.

Example 1

Preparation of Composition for Forming Adhesive Layer

Under an inert gas atmosphere, 2-ethylhexyl acrylate (95 parts by weight), acrylic acid (5 parts by weight) and benzoyl peroxide (0.2 part by weight) were subjected to solution polymerization in ethyl acetate at 60° C. to give an acrylic adhesive solution.

The acrylic adhesive, an organic liquid component (isopropyl palmitate), and a drug (isosorbide dinitrate, therapeutic drug for angina pectoris) were mixed at a weight ratio of 43:40:17 in the presence of ethyl acetate. Furthermore, CORONATE HL (manufactured by Nippon Polyurethane Industry Co., Ltd.) was mixed as a crosslinking agent in 0.15 part by weight relative to 100 parts by weight of acrylic adhesive solid content to give a composition for forming an adhesive layer.

<Preparation of Adhesive Sheet>

The above-mentioned composition was applied to an easy-release surface of a release liner (thickness 75 μm) made of PET such that the thickness of the adhesive layer after drying was 200 μm, and dried in a drying oven (100° C.) to give a release liner comprising an adhesive layer. The surface where the adhesive layer had been formed was laminated on a PET film surface of a support which is a laminate (thickness of whole support 35 μm) of a polyethylene film (thickness 20 μm), an aluminum thin film layer and a PET film (thickness 15 μm) by pressure-bonding to give an adhesive sheet. The adhesive sheet was tightly sealed in a package material (outer size 600 mm×250 mm, inner size 580 mm×230 mm) with an outer layer made of a 12 μm-thick PET film and an inner layer made of a 30 μm-thick polyacrylonitrile based resin film, left standing in a thermostat at 70° C. for 48 hr to promote a crosslinking reaction of the adhesive layer, and an adhesive sheet for punching out a patch preparation was prepared.

<Preparation of Water Resistant Patch Preparation>

Using a press mold (external size 33.5 mm×33.5 mm, internal size 27.5 mm×27.5 mm, height of convex part 5 mm) having a flat plane shape outlined by the shapes of two coaxial substantial squares, the surface of a support of the adhesive sheet for punching out a patch preparation was heated and pressed (heating temperature: 120° C., pressure: $2.9 \times 10^6$ N/m$^2$, heating-pressing time: 1 second, distance between press mold and stand: 160 μm). Furthermore, using the same type of a press mold, the same part was pressed again (temperature: 25° C., pressure: $2.9 \times 10^6$ N/m$^2$, pressing time: 3 seconds, distance between press mold and stand: 110 μm). A patch preparation and a release liner were simultaneously punched out from the heated and pressed adhesive sheet using a Thomson blade such that the heated and pressed area corresponds to the peripheral part of the patch preparation to be obtained later, whereby the water resistant patch preparation of the present invention was obtained. The obtained water resistant patch preparation was a substantial square with a one side length of about 30.5 mm as an outline, which had a band-shaped peripheral part (width about 1.5 mm) in all peripheral parts, and a substantially square central part inside the peripheral part. (external shape: square of about 30.5 mm, shape of central part: square of about 27.5 mm, peripheral part: about 1.5 mm width, void: about 1.4 mm width)

Example 2

Preparation of Composition for Forming Adhesive Layer

Polyisobutylene 1 having a high molecular weight (viscosity average molecular weight 4,000,000), polyisobutylene 2 having a low molecular weight (viscosity average molecular weight 80,000), a tackifier (alicyclic saturated hydrocarbon resin, softening point 100° C. (ring and ball method)), an organic liquid component (isopropyl palmitate), and a drug (tulobuterol, bronchodilator) were mixed at a weight ratio of 15:20:20:35:10 in the presence of hexane to give a composition for forming an adhesive layer.

<Preparation of Adhesive Sheet>

The above-mentioned composition was applied to an easy-release surface of a PET release liner (thickness 75 µm) such that the thickness of an adhesive layer after drying was 200 µm, and dried in a drying oven (70° C.) to give a release liner having an adhesive layer. The surface having the adhesive layer was laminated on a support, which is a PET film having a thickness of 12 µm, by pressure-bonding to give an adhesive sheet for punching out a patch preparation.

<Preparation of Water Resistant Patch Preparation>

Using a press mold (external size 33.5 mm×33.5 internal size 27.5 mm×27.5 mm, height of convex part 5 mm) having a flat plane shape outlined by the shapes of two coaxial substantial squares, the surface of a support of the adhesive sheet for punching out a patch preparation was heated and pressed (heating temperature: 120° C., pressure: $2.9 \times 10^6$ N/m$^2$, heating-pressing time: 1 second, distance between press mold and stand: 130 µm). Furthermore, using the same type of a press mold, the same part was pressed again (temperature: 25° C., pressure: $2.9 \times 10^6$ N/m$^2$, pressing time: 3 seconds, distance between press mold and stand: 90 µm). A patch preparation and a release liner were simultaneously punched out from the heated and pressed adhesive sheet using a Thomson blade such that the heated and pressed area corresponds to the peripheral part of the water resistant patch preparation to be obtained later, whereby the water resistant patch preparation of the present invention was obtained. The obtained water resistant patch preparation was a substantial square with a one side length of about 30.5 mm as an outline, which had a band-shaped peripheral part (width about 1.5 mm) in all peripheral parts, and a substantially square central part inside the peripheral part. (external shape: square of about 30.5 mm, shape of central part: square of about 27.5 mm, peripheral part: about 1.5 mm width, void: about 1.3 mm width)

Comparative Example 1

In the same manner as in Example 1 except that the second pressing step was omitted, a patch preparation was obtained. (external shape: square of about 30.5 mm, shape of central part: square of about 27.5 mm, peripheral part: about 1.5 mm width)

Comparative Example 2

In the same manner as in Example 1 except that the first and second pressing steps were omitted, and the adhesive layer in the lateral end of the patch preparation after punching out was scraped out with a pincet, a patch preparation was obtained. (external shape: square of about 30.5 mm, shape of central part: square of about 27.7 mm, void: about 1.4 mm width)

Comparative Example 3

In the same manner as in Example 1 except that the first and second pressing steps were omitted, a patch preparation was obtained.
(external shape: square of about 30.5 mm, shape of central part: square of about 30.5 mm, peripheral part: none)

Comparative Example 4

In the same manner as in Example 2 except that the second pressing step was omitted, a patch preparation was obtained. (external shape: square of about 30.5 mm, shape of central part: square of about 27.5 mm, peripheral part: about 1.5 mm width)

Comparative Example 5

In the same manner as in Example 2 except that the first and second pressing steps were omitted, and the adhesive layer in the lateral end of the patch preparation after punching out was scraped out with a pincet, a patch preparation was obtained. (external shape: square of about 30.5 mm, shape of central part: square of about 27.9 mm, void: about 1.3 mm width)

Comparative Example 6

In the same manner as in Example 2 except that the first and the second pressing steps were omitted, a patch preparation was obtained.
(external shape: square of about 30.5 mm, shape of central part: square of about 30.5 mm, peripheral part: none)

The schematic sectional view of the patch preparations of Examples 1 and 2 is shown in FIG. 9(a), that of Comparative Examples 1 and 4 is shown in FIG. 9(b), that of Comparative Examples 2 and 5 is shown in FIG. 9(c), and that of Comparative Examples 3 and 6 is shown in FIG. 9(d).

The patch preparations of Examples 1 and 2, and Comparative Examples 1-6 were evaluated for the following evaluation items.

Experimental Example 1

Evaluation of Shape of Patch Preparation

The patch preparations were cut with a razor for trimming, the cross section thereof was observed with a digital microscope (Keyence Corporation, VHX-600, magnification 1000 times), and the thickness of the adhesive layer in the peripheral part and central part was measured. Furthermore, the cross sectional shape of the lateral end of the adhesive layer was observed, and the distance from the lateral end of the support to a part of the adhesive layer, which was located nearest to the central part, was measured. The results are shown in Table 1.

Experimental Example 2

Evaluation of Release Rate of Drug into Water from Preparation Periphery

The patch preparation was adhered onto a rotary cylinder with the support located outside, the whole cylinder and the patch preparation on the cylinder were immersed in a test solution (distilled water at 40° C., 400 mL), and the cylinder was rotated at a rate of 50 rpm in the test solution. After 30 min, the test solution was recovered, and the drug in the recovered test solution was quantified by an HPLC method, and the amount of drug release was calculated. The drug release rate was calculated by dividing the drug release amount by the drug content of the patch preparation quantified by the HPLC method. The results are shown in Table 1.

TABLE 1

| | width of peripheral part (mm) | thickness of adhesive layer (μm) | | cross sectional shape of adhesive layer side face | | drug release rate (%) after 30 min |
|---|---|---|---|---|---|---|
| | | peripheral part | central part | shape | distance (mm) from lateral end of support to a part of adhesive layer, located nearest to central part | |
| Ex. 1 | 1.5 | 50 | 200 | concave form | 1.4 | 0.38 |
| Comp. Ex. 1 | 1.5 | 50 | 200 | flat-topped | 0 | 1.77 |
| Comp. Ex. 2 | 0 | 200 | 200 | concave form | 1.4 | 2.05 |
| Comp. Ex. 3 | 0 | 200 | 200 | flat-topped | 0 | 4.93 |
| Ex. 2 | 1.5 | 40 | 200 | concave form | 1.3 | 0.26 |
| Comp. Ex. 4 | 1.5 | 40 | 200 | flat-topped | 0 | 1.08 |
| Comp. Ex. 5 | 0 | 200 | 200 | concave form | 1.3 | 1.32 |
| Comp. Ex. 6 | 0 | 200 | 200 | flat-topped | 0 | 2.06 |

As is clear from Table 1, the drug release rate after immersing in water for 30 min was remarkably smaller in Examples 1 and 2 than in any Comparative Example. The resulting effects are considered to be attributable to the following:
(1) the thickness of the adhesive layer in the peripheral part is smaller than that of the adhesive layer in the central part,
(2) the adhesive layer lateral end in the peripheral part of the patch preparation is located inside the support lateral end.

INDUSTRIAL APPLICABILITY

The water resistant patch preparation of the present invention can suppress cold flow and elution of components such as a drug and the like from the exposed lateral end of the adhesive layer when it is soaked in water for a long time such as a bath and the like.

This application is based on a patent application No. 2009-207563 filed in Japan (filing date: Sep. 8, 2009), the contents of which are incorporated in full herein by this reference.

EXPLANATION OF SYMBOLS 1 central part
2 peripheral part
3 void
11 support
12 adhesive layer
12a thick film part
12b transition part
12c thin film part
13 release liner
21 package
22 skin
23 clothes
24 patch preparation
31 water
41 void
101 press mold
102 convex part of press mold
103 second-press mold
104 convex part of second-press mold
110 support
120 adhesive layer
121 adhesive central part
122 adhesive peripheral part
123 void
130 release liner

The invention claimed is:

1. A water resistant patch preparation comprising (a) a support with at least one surface and (b) an adhesive layer containing a drug, wherein
the water resistant patch preparation has a central part and a peripheral part surrounding the central part,
the adhesive layer is disposed on one surface of the support in the central part and in a portion of the peripheral part, wherein the one surface of the support containing the adhesive layer has at least a portion in the peripheral part that is free of the adhesive layer,
the portion of the peripheral part of the support that is free of the adhesive layer has a width of 0.5-5 mm, and
the adhesive layer in the peripheral part has a thickness that is smaller than a thickness of the adhesive layer in the central part.

2. The water resistant patch preparation according to claim 1, wherein the thickness of the adhesive layer in the peripheral part is 1.5-150 μm.

3. The water resistant patch preparation according to claim 1, wherein the adhesive layer in the central part has a maximum thickness, and a difference between the maximum thickness of the adhesive layer in the central part and the thickness of the adhesive layer in the peripheral part is 20-2000 μm.

4. The water resistant patch preparation according to claim 1, wherein the adhesive layer in the peripheral part is a band with a width of 0.5-5 mm.

5. The water resistant patch preparation according to claim 1, wherein the adhesive layer comprises an organic liquid component.

6. The water resistant patch preparation according to claim 1, wherein the adhesive layer is crosslinked.

7. The water resistant patch preparation according to claim 1, wherein the support comprises a resin film and the resin film has a thickness of 1-45 μm.

8. The water resistant patch preparation according to claim 1, wherein the support comprises a thermoplastic resin.

9. The water resistant patch preparation according to claim 8, wherein the thermoplastic resin comprises poly(ethylene terephthalate).

10. The water resistant patch preparation according to claim 1, wherein a release liner is further laminated on the adhesive layer.

11. The water resistant patch preparation according to claim 2, wherein a release liner is further laminated on the adhesive layer.

12. The water resistant patch preparation according to claim 3, wherein a release liner is further laminated on the adhesive layer.

13. The water resistant patch preparation according to claim 4, wherein a release liner is further laminated on the adhesive layer.

14. The water resistant patch preparation according to claim 5, wherein a release liner is further laminated on the adhesive layer.

15. The water resistant patch preparation according to claim 6, wherein a release liner is further laminated on the adhesive layer.

16. The water resistant patch preparation according to claim 7, wherein a release liner is further laminated on the adhesive layer.

17. The water resistant patch preparation according to claim 8, wherein a release liner is further laminated on the adhesive layer.

18. The water resistant patch preparation according to claim 9, wherein a release liner is further laminated on the adhesive layer.

* * * * *